United States Patent
Piantoni et al.

(10) Patent No.: US 10,821,032 B2
(45) Date of Patent: Nov. 3, 2020

(54) DEVICE FOR CUTTING A WEB OF MATERIAL

(71) Applicants: GDM S.p.A., Bologna (IT); UNIVERSITA' DEGLI STUDI DI BERGAMO, Bergamo (IT)

(72) Inventors: Matteo Piantoni, Albino (IT); Valerio Soli, Bologna (IT); Davide Russo, Florence (IT); Paolo Carrara, Sovere (IT)

(73) Assignees: GDM S.P.A., Bologna (IT); UNIVERSITA' DEGLI STUDI DI BERGAMO, Bergamo (IT)

( * ) Notice: Subject to any disclaimer, the term of this patent is extended or adjusted under 35 U.S.C. 154(b) by 726 days.

(21) Appl. No.: 15/304,794

(22) PCT Filed: Apr. 14, 2015

(86) PCT No.: PCT/IB2015/052696
§ 371 (c)(1),
(2) Date: Oct. 17, 2016

(87) PCT Pub. No.: WO2015/159207
PCT Pub. Date: Oct. 22, 2015

(65) Prior Publication Data
US 2017/0035618 A1 Feb. 9, 2017

(30) Foreign Application Priority Data
Apr. 18, 2014 (IT) .............................. BO2014A0227

(51) Int. Cl.
*B23K 26/08* (2014.01)
*A61F 13/15* (2006.01)
(Continued)

(52) U.S. Cl.
CPC .. *A61F 13/15723* (2013.01); *A61F 13/15764* (2013.01); *B23K 26/032* (2013.01);
(Continued)

(58) Field of Classification Search
CPC .......... A61F 13/15723; A61F 13/15764; A61F 2013/15821; B23K 26/082; B23K 26/032;
(Continued)

(56) References Cited

U.S. PATENT DOCUMENTS

| 5,444,212 A | * | 8/1995 | MacNaughton | B23K 26/0846 219/121.7 |
| 5,690,846 A | * | 11/1997 | Okada | B23K 26/0853 219/121.71 |
| 2005/0061781 A1 | | 3/2005 | Jense | |

FOREIGN PATENT DOCUMENTS

| CN | 1460589 A | 12/2003 |
| EP | 0549357 A1 | 6/1993 |

(Continued)

OTHER PUBLICATIONS

Japanese Office Action dated Mar. 14, 2019 for counterpart Japanese Patent Application No. JP 2016-563024.
(Continued)

*Primary Examiner* — Chee-Chong Lee
(74) *Attorney, Agent, or Firm* — Shuttleworth & Ingersoll, PLC; Timothy Klima (57) ABSTRACT

A device for cutting a web of material comprises movement means for moving a web of material to be cut, defining a feed path for the web at least partly rotatable about a central axis and equipped with at least one conveyor mounted around the central axis, at least one cutting head equipped with a laser source and an optical system configured to direct the laser beam towards a cutting zone, where the optical system of the cutting head comprises at least one directing (Continued)

member located inside the conveyor to direct the laser beam away from the central axis towards the cutting zone.

7 Claims, 4 Drawing Sheets (51) Int. Cl.
  *B23K 26/082* (2014.01)
  *B23K 26/03* (2006.01)
  *B23K 103/00* (2006.01)
(52) U.S. Cl.
  CPC ............ *B23K 26/08* (2013.01); *B23K 26/082* (2015.10); *B23K 26/0846* (2013.01); *A61F 2013/15821* (2013.01); *B23K 2103/40* (2018.08)
(58) Field of Classification Search
  CPC . B23K 26/08; B23K 26/0846; B23K 2103/40

USPC .................................................... 219/121.67
See application file for complete search history.

(56) References Cited

FOREIGN PATENT DOCUMENTS

| | | |
|---|---|---|
| JP | 2013256109 A | 12/2013 |
| WO | WO2008015550 A2 | 2/2008 |

OTHER PUBLICATIONS

Office Action issued by the Chinese Patent Office dated Oct. 31, 2018 for counterpart Chinese Patent Application No. CN201580020282. 4.

International Search Report and Written Opinion dated Aug. 14, 2015 for counterpart PCT Application No. PCT/IB2015/052696.

* cited by examiner

FIG. 4c

DEVICE FOR CUTTING A WEB OF MATERIAL

This application is the National Phase of International Application PCT/IB2015/052696 filed Apr. 14, 2015 which designated the U.S.

This application claims priority to Italian Patent Application No. BO2014A000227 filed Apr. 18, 2014, which application is incorporated by reference herein.

TECHNICAL FIELD

This invention relates to a device for laser cutting a web of material, preferably a continuous web.

More specifically, this invention applies to the manufacture of sanitary underwear such as baby nappies, sanitary towels or the like.

BACKGROUND ART

These sanitary articles typically comprise an absorbent pad which is normally sandwiched between a permeable inner layer of non-woven fabric and an impermeable outer layer of polyethylene.

The manufacture of such articles involves the formation initially of a continuous web incorporating the aforementioned layers, then shaping the web and finally separating the web into single items ready for packaging.

Shaping consists mainly in the cutting of leg contours and, more generally, serves to give the article an outline appropriate for the specified use.

Prior art devices used for this type of operation comprise a rotating drum, around which the web is looped partially as it advances in a predetermined direction, and a laser cutting head that operates on the web in the course of its passage over the drum. Laser cutting heads are especially suitable for processes used in the manufacture of sanitary underwear products, by virtue of their low maintenance requirements and their ease of control and adjustment, especially when compared with rotary blade cutter systems adopted in this same technical field, which require frequent replacement of the blades, or at all events, frequent sharpening of the blades.

While the pros of such an application are evident, one disadvantage of using laser cutting is, without doubt, that connected with the movement of the cutting head and/or of the optical systems, since the very high speed of web feed and the mass production of these articles involves the use of extremely rapid reciprocating drives and the consequent need to move masses which are all but negligible and which undergo very significant acceleration.

In other words, one of the major disadvantages of this technology is due to the high inertia loads involved, requiring high-powered (and high-cost) drive systems and very high-strength structures.

A further solution of the prior art is disclosed in document EP0549357, which illustrates the use a laser cutting head within a rotary drum, by directing the laser beam on the inner surface of the drum, carved, in order to make cuts or incisions on the web translating with the drum.

In particular, said document specifies that the cutting head comprises a fixed directioning element positioned at the center of the drum to deflect the laser beam towards the drum surface, widening it so as to cover the drum entire width.

In this light, additional mirrors are placed inside the drum to intercept the portions of the laser refracted/reflected diverting them again on the surface.

Disadvantageously, this solution requires high power laser sources as the fixed position of the deflector element implies the need to complete the cut instantaneously or, at the most, to stop the movement of the drum during the cut, which is clearly undesirable in the technical field of interest.

Moreover, it is not to be underestimated also the problem of the security, which is particularly critical in light of the widespread distribution of the laser beam of EP0549357, which is designed to cover the entire width of the drum resulting active only in correspondence of the notches and being therefore reflected/refracted for the greater part.

DISCLOSURE OF THE INVENTION

In light of the above, the primary technical purpose of this invention is to devise a device for laser cutting a web of material and capable of overcoming the above mentioned disadvantages.

In the context of this technical purpose, one important aim of the invention is to provide a device for laser cutting a web of material and capable of reducing the resources necessary for cutting in motion.

A further aim of the invention is to devise a device for laser cutting a web of material where the movements associated with the cutting head are minimized.

The technical purpose and aims specified are substantially achieved by a device for laser cutting a web of material comprising the technical features set out in claim 1.

BRIEF DESCRIPTION OF DRAWINGS

Further features and advantages of this invention are more apparent in the non-limiting description of a preferred but non-exclusive embodiment of a device for laser cutting a web of material, as illustrated in the accompanying drawings, in which.

DETAILED DESCRIPTION OF PREFERRED EMBODIMENTS OF THE INVENTION

With reference to the accompanying drawings, the numeral 1 denotes a device for laser cutting a web 2 of material.

Preferably, the device 1 is fitted in a machine for making sanitary underwear such as baby nappies or sanitary towels.

The device thus comprises an unwinder (not illustrated) at which a web 2, preferably continuous and padded, is made, for example by juxtaposing a first layer of permeable material with a second layer of impermeable material and interposing between the two a portion of absorbent material, not illustrated, constituting the padding. This operation is done, for example, by two feed rollers and a device of known type, not illustrated in the drawings, for adding the pad.

It should be noted, however, that the cutting device according to this invention may be used to divide and cut any component, even an accessory one, of the sanitary article, provided it can be fed from a web of material, irrespective of its composition.

Thus, the continuous web 2 is made to advance by means of suitable movement means 3 configured to impart motion to the web 2 of material to be cut.

More precisely, the movement means 3 by which the web 2 of material to be cut is made to advance define for the web 2 a feed path "P" which is at least partly rotatable about a central axis, hereinafter referred to as central axis "A". The central axis "A" is thus transversal to the web 2.

More in detail, the movement means 3 comprise at least a conveyor 4 mounted around the central axis "A" and defining an at least partly curved cutting zone "Z".

Thus, the conveyor 4 is structured to define in the feed path "P" a curve whose concavity faces the central axis "A".

Preferably, as will become clearer as this description continues, the conveyor 4 comprises at least a drum 5 rotatable about its axis of rotation which preferably corresponds to the central axis "A" (FIGS. 1, 2, 3a, 3b).

Figures 4A, 4B, 4C:
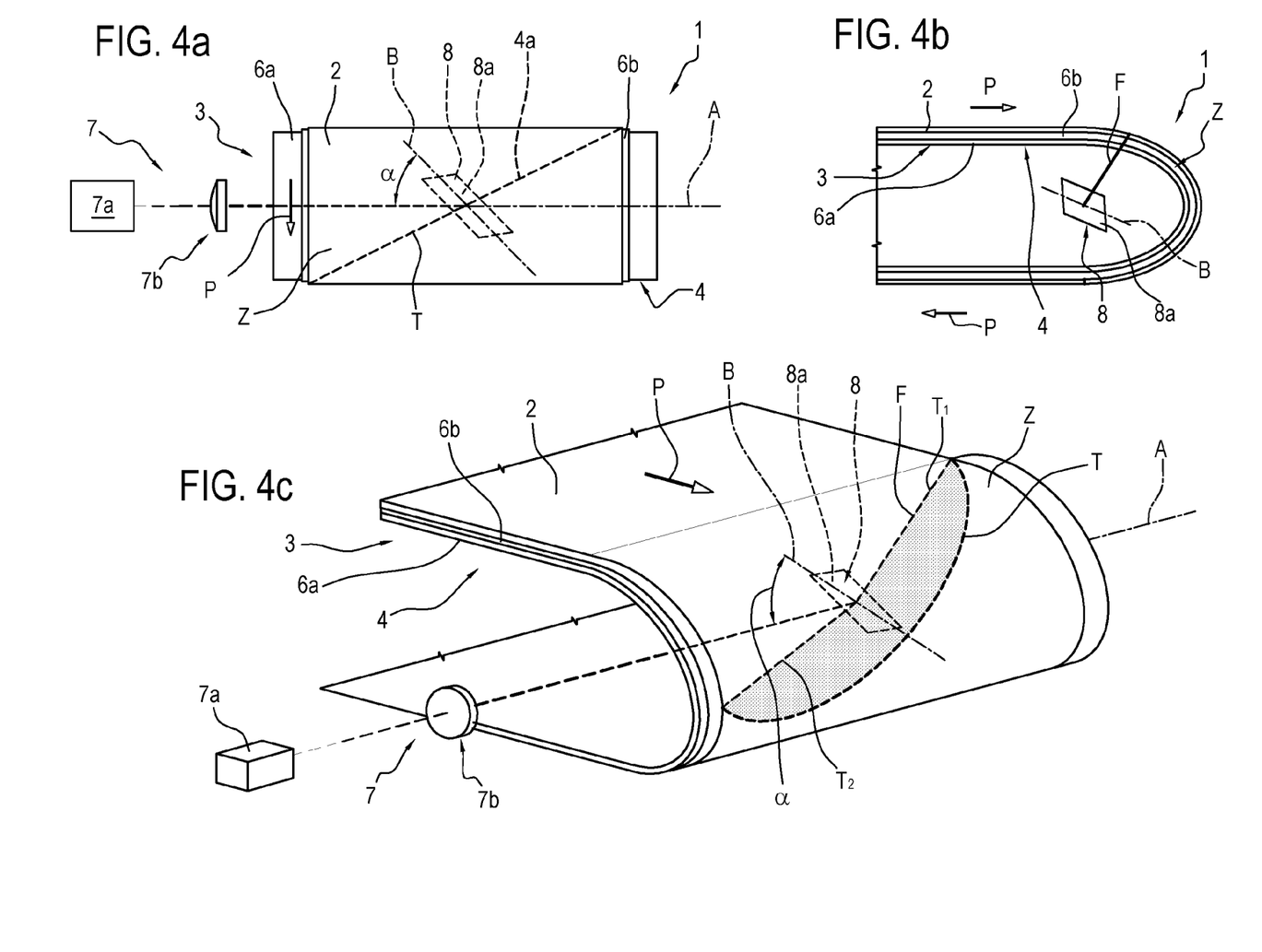
FIGS. 4a-4c are a schematic front view, a schematic side view and a perspective view, respectively, of a fourth embodiment of the device according to this invention for laser cutting a web of material.

Alternatively, the conveyor 4 may be defined by a curved central core 6a slidably associated with a sliding belt 6b or the like (FIGS. 4a-4c).

To guarantee processing precision, the device is equipped with tensioning means (not illustrated) preferably operatively located both upstream and downstream of the conveyor.

More preferably, the tensioning means define for the web 2 (at least partly) a feed unit 12 and a pickup unit 13, respectively, associated with the conveyor 4.

The feed unit 12 is operatively located upstream of the conveyor 4 to direct the web 2, that is, the feed path "P" thereof, towards the conveyor at a predetermined entry angle.

Similarly, the pick-up unit 13 is operatively located downstream of the conveyor 4 to pick up the web 2, that is, to determine its feed path "P" on leaving the conveyor 4, at a predetermined exit angle.

In order to cut the material, the device 1 also comprises a laser cutting head 7, equipped with a laser source 7a configured to generate a laser beam "F", and an optical system 7b configured to direct the laser beam "F" towards the cutting zone "Z".

According to the invention, the optical system 7b of the cutting head 7 comprises at least one directing member 8 located inside the conveyor 4 to direct the laser beam "F" away from the central axis "A" towards the cutting zone "Z".

In other words, the directing member 8 faces the concavity defined by the conveyor 4. More precisely, the directing member 8 is located in the proximity of the central axis "A".

It should be noted that the directing member 8 is preferably a mirror 8a or lens operatively associated with the laser source 7a by a system of mirrors 9 or lenses.

In other words, the directing member 8 preferably defines an end element of the cutting head 7 from which the laser beam "F" is projected in the direction of the material to be cut.

The directing member 8 may also be constituted by a metallic component made of molybdenum, aluminium or copper.

Advantageously, the possibility of moving a single directing member 8 (that is, a single mirror 8a) located inside the conveyor 4 allows considerably reducing not only the dimensions of the device but also the inertias involved during cutting.

In this regard, the directing member 8 is preferably rotatable about its axis of rotation "B" and is oriented (or orientable) in such a way that the laser beam "F" defines on the web 2 a cutting line "T" transversal to the feed path "P" of the web 2 itself.

More precisely, the directing member 8 is rotatable at least between a first angular, start-of-cutting position "T1" and a second angular, end-of-cutting position "T2".

Thus, the directing member 8 is mounted along an optical path of the laser beam "F" to intercept and deflect it in the direction of the cutting zone "Z" starting from the inside of the conveyor 4 and away from the central axis "A".

In order to make a cut which is transversal to the feed path "P" of the web 2 along the conveyor 4, the directing member 8 is rotatable about its axis of rotation "B".

Advantageously, using the movement of the web 2 along its longitudinal direction, imparted by the conveyor 4 (that is, along the feed path "P"), it is sufficient for the directing member 8 to be made to rotate about its axis of rotation "B" to obtain a cut which is transversal to that direction and to easily control cutting along both axes.

It should be noted that positioning the directing member 8 inside the conveyor 4 considerably reduces the change of distance between the directing member 8 itself and the cutting zone Z, thereby allowing a reduction in the movements of the components and, consequently, in the stresses on the structure of the device.

It should be noted that to allow correctly cutting the web 2 without impairing the structure of the device 1, the conveyor 4 (which constitutes a curved feed surface for the web 2), is equipped at the cutting zone "Z", with at least one permeable portion 4a permeable to the laser beam "F" and facing the directing member 8, so as to allow the laser beam "F" to pass through the feed surface.

In other words, the conveyor 4 is equipped with at least one laser transparent portion shaped at least like the cutting line to allow the laser beam "F" to pass from the inside of the conveyor 4, in which the directing member 8 is situated, to the outside of the conveyor 4, on which the web 2 rests (and thus constituting the feed surface for the web 2).

More in detail, the permeable portion 4a made in the conveyor 4 extends at least between one end, corresponding to the first angular (or start-of-cutting) position "T1" of the directing member 8, and a second end, corresponding to the second angular (or end-of-cutting) position "T2" of the directing member 8.

Depending on the embodiment, the permeable portion 4a may differ in structure and shape.

Figure 1:
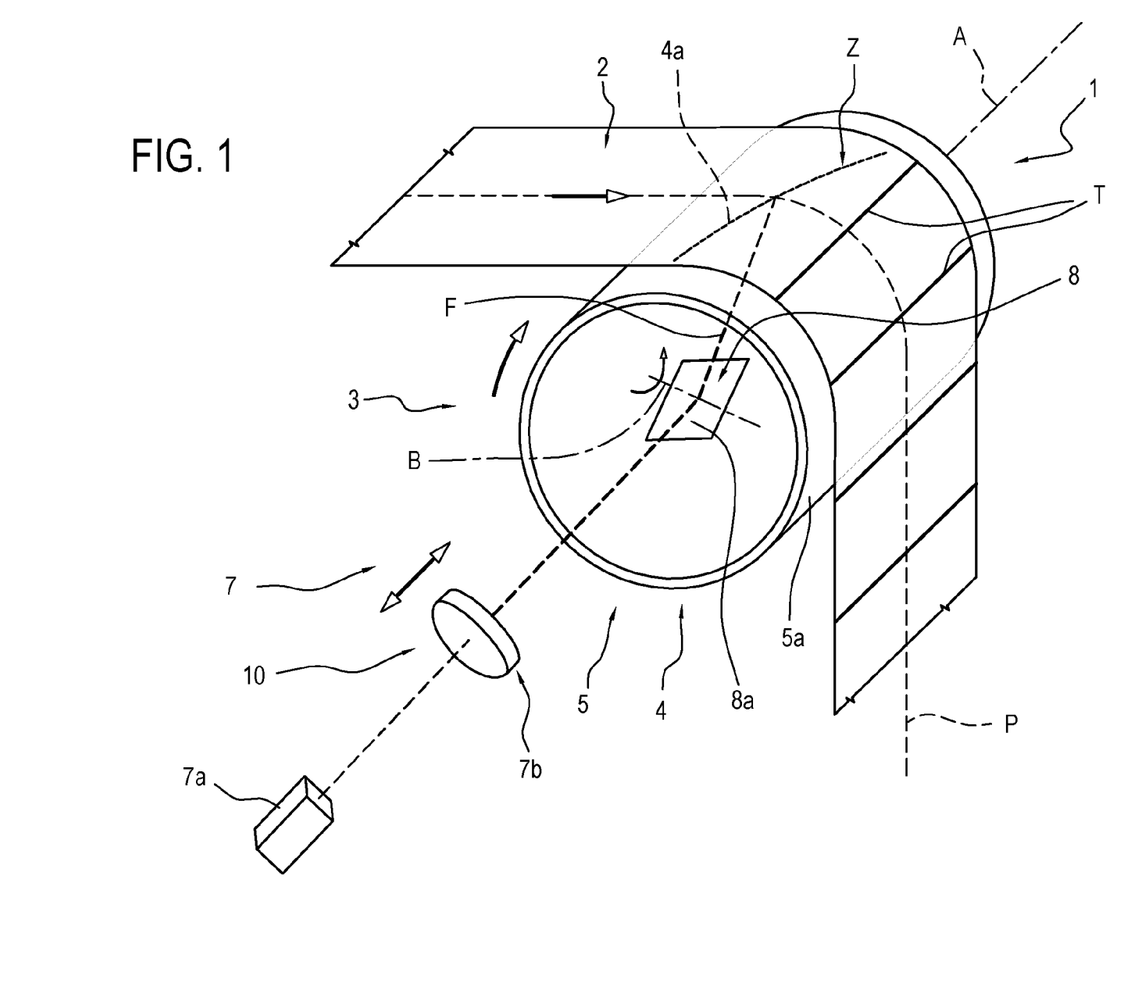
FIG. 1 shows a schematic view of a first embodiment of the device according to this invention for laser cutting a web of material.

In the embodiment illustrated in FIG. 1, the permeable portion 4a is defined by a through opening. More precisely, the opening is a slot extending transversely to the feed path "P". More precisely, in this embodiment (as in other preferred embodiments) the slot extends in a direction substantially parallel to the central axis "A".

Alternatively, the permeable portion 4a might be defined by an insert or window which is transparent to the laser beam "F".

Provided below by way of example (non exhaustive) are some lists of materials which can be used for this purpose, according to the type of laser:

| CO2 LASER: | |
| --- | --- |
| Barium fluoride | $BaF_2$ |
| Zinc selenide | ZnSe |
| Gallium arsenide | GaAs |
| Germanium | Ge |
| Cadmium telluride | CdTe |
| Cadmium magnesium telluride | CdMgTe |
| Cadmium manganese mercury telluride | CdMnHgTe |
| Cadmium manganese telluride | CdMnTe |
| Amorphous quartz | $SiO_2$ |
| Potassium bromide | KBr |
| Potassium chloride | KCl |
| Silver bromide | AgBr |
| Silver chloride | AgCl |
| Sodium chloride | NaCl |
| Thallium bromo-iodide | TlBr-TlI |
| DIODE: | |
| Barium fluoride | $BaF_2$ |
| Zinc selenide | ZnSe |
| Gallium arsenide | GaAs |
| Germanium | Ge |
| Cadmium magnesium telluride | CdMgTe |
| Cadmium manganese mercury telluride | CdMnHgTe |
| Cadmium manganese telluride | CdMnTe |
| Amorphous quartz | $SiO_2$ |
| Potassium bromide | KBr |
| Potassium chloride | KCl |
| Silver bromide | AgBr |
| Silver chloride | AgCl |
| Sodium chloride | NaCliBr |
| Thallium bromo-iodide | TlBr |
| Borosilicate glass | BK-7 |
| Calcium fluoride | $CaF_2$ |
| Magnesium fluoride | $MgF_2$ |
| Sapphire | $Al_2O_3$ |
| QCL: | |
| Barium fluoride | $BaF_2$ |
| Zinc selenide | ZnSe |
| Gallium arsenide | GaAs |
| Germanium | Ge |
| Cadmium magnesium telluride | CdMgTe |
| Cadmium manganese mercury telluride | CdMnHgTe |
| Cadmium manganese telluride | CdMnTe |
| Amorphous quartz | $SiO_2$ |
| Potassium bromide | KBr |
| Potassium chloride | KCl |
| Silver bromide | AgBr |
| Silver chloride | AgCl |
| Sodium chloride | NaCliBr |
| Thallium bromo-iodide | TlBr |
| Cadmium telluride | CdTe |
| Calcium fluoride | $CaF_2$ |
| Magnesium fluoride | $MgF_2$ |
| Sapphire | $Al_2O_3$ |
| Silicon | Si |

In these embodiments, the device 1 preferably comprises means for cleaning the insert or window, configured to remove the dirt produced by the sublimation of the fibrous material (i.e. the material of the web).

As mentioned previously, the directing member 8 is preferably rotatable (or, in any case, movable) inside the conveyor in order to direct the laser beam "F" along a predetermined direction.

Preferably, the device 1 is equipped with motion transmission means 9, of mechanical or electro-mechanical type, operatively interposed between the movement means 3 and the directing member 8 to correlate a movement of the movement means 3 along the feed path "P" with the rotation of the directing member 8 about its axis of rotation "B".

Advantageously, there is thus no need for a specific drive for the cutting head 7, but it is possible to use only the rotation of the conveyor 4 (or more in general, the advancing motion of the movement means 3) to produce and control the movement of the directing member 8.

Preferably, the transmission means 9 are defined by a system of toothed wheels and/or belts (not illustrated).

Alternatively, the transmission means 9 might comprise a galvo (electro-mechanical) system.

The galvo system comprises a limited-rotation DC motor to drive the laser beam "F" directing member 8.

Preferably, an internal position sensor is provided for closed-loop control of the motor by means of a signal proportional to the rotation position of the motor shaft.

Advantageously, such a system allows digital control which is rapid and modifiable remotely.

Alternatively, or in conjunction, the directing member 8 might be attached to the conveyor 4 in such a way as to rotate as one therewith.

For example, in the embodiment shown in FIG. 1, the directing member is attached to the drum 5 to rotate therewith about the central axis "A", but also rotates about its own axis of rotation "B" in order to make a cutting line "T" transversal to the feed direction.

In this embodiment (FIG. 1), the optical system 7*b* of the cutting head 7 comprises at least one focusing unit 10 operatively located upstream of the directing member 8 and able to move translationally in a straight line between a position close to the directing member 8, where the focal point of the laser beam "F" is distal from the directing member 8 itself, and a position away from the directing member 8, where the focal point of the laser beam "F" is proximal to the directing member 8 itself.

Advantageously, the linear movement of the focusing unit 10 allows compensating for variations in effective distance between the directing member 8 and the cutting zone "Z".

In effect, in this embodiment, the conveyor 4 is defined by a cylindrical drum 5 rotatable about its longitudinal axis, defining the central axis "A". The directing member 8 is preferably located at the central axis "A".

As mentioned above, in order to make a cut which is transversal to the feed path "P" of the web 2, the directing member 8 rotates about an axis of rotation "B" which is transversal to the central axis "A", thus, during cutting, varying its distance from the cutting zone "Z" itself, that is, from the point on the web 2 where cutting occurs.

It should be noted that since the axis of rotation "B" is incident upon the central axis "A" of the drum 5, the variation in the distance between the directing member 8 and the cutting zone "Z" during cutting is much more limited than in the prior art (where cutting is effected from the outside of the conveyor).

In order to completely eliminate any axial movement of the optical system 7*b*, the feed path "P" and the axis of rotation "B" of the directing member 8 are preferably positioned (FIGS. 2, 3*a*, 3*b*, 4*a*-4*c*) in such a way that for each angular position of the directing member 8 (at least between the first angular position "T1" and the second "T2") a line joining the directing member 8 itself and the feed surface for the web 2 travelled by the laser beam "F" is substantially constant.

More precisely, the movement means 3 and the directing member 8 are positioned in such a way that for each angular position of the directing member 8, the optical path followed by the laser beam "F" between the directing member 8 and the feed surface for the web 2 is substantially constant in length.

In other words, the feed means 3 (that is, the conveyor 4) and the optical system 7*b* are structured in such a way that the optical path of the laser beam "F" defines, between the first angular position "T1" and the second "T2" of the directing member 8, a circular sector, that is, a portion of a circle (whose vertex is preferably inside the directing member 8).

Advantageously, that way, the distance between the directing member 8 and the cutting zone "Z" (that is, the feed surface for the web 2) remains constant without having to adjust the focal distance (and thus without the need for axial movements of the optical system 7b).

In accordance with the above, in a first embodiment (FIGS. 3a-3c), where the conveyor 4 is again defined at least partly by a cylindrical drum 5 rotatable about the central axis "A", the cutting zone "Z" is defined on a peripheral surface 5a of the drum 5 itself.

Figure 3A:
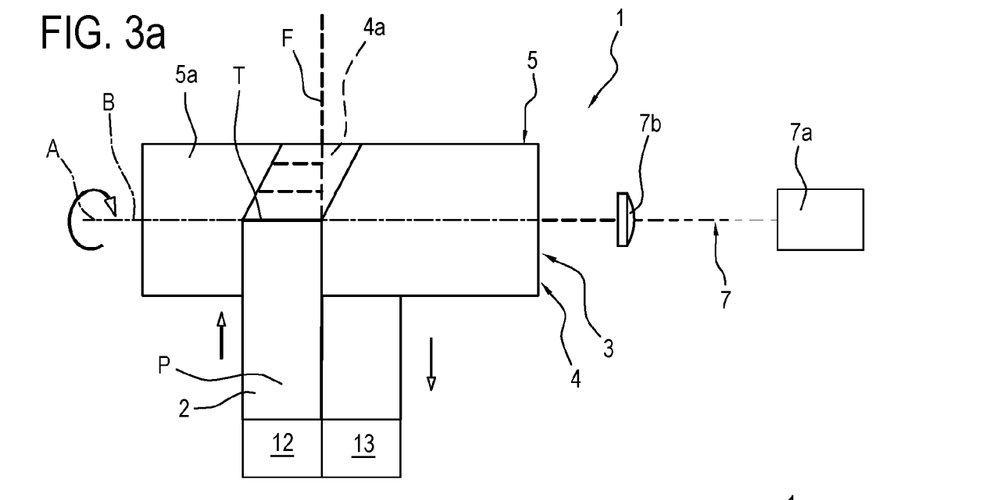
FIGS. 3a-3c illustrate a third embodiment of the device according to this invention for laser cutting a web of material in schematic top and side views, respectively.
Figure 3B:
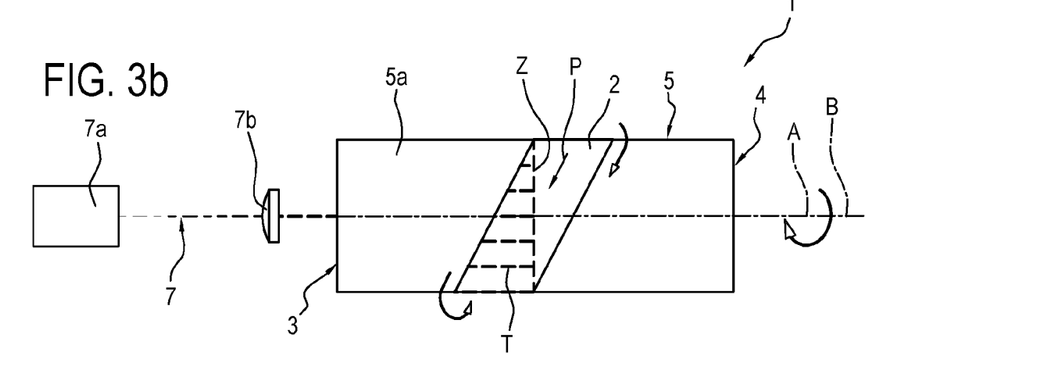
Figure 3C:
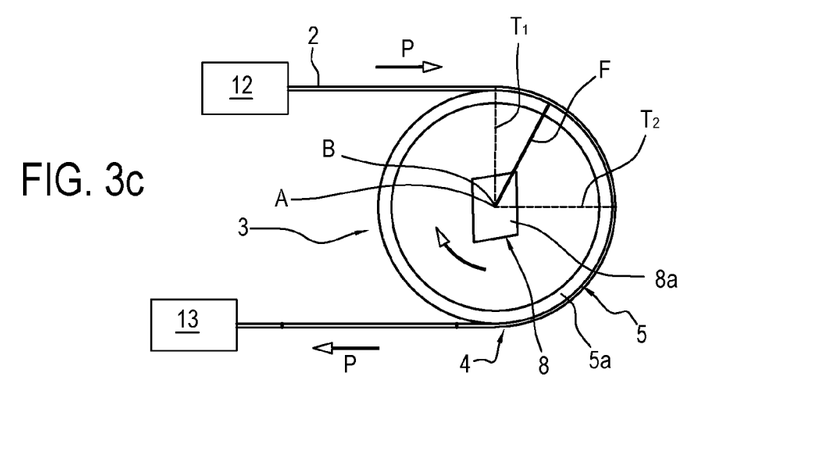

In this embodiment, the directing member 8 is located at the central axis "A" of the drum 5 and is oriented in such a way that, between the first angular position "T1" and the second "T2" of the directing member 8, the laser beam "F" remains in a plane at right angles to the central axis "A".

Thus, the directing member 8 is rotatable about the central axis "A".

In other words, in this embodiment, the directing member 8 (that is, the mirror) is positioned in such a way as to direct the laser beam "F" in a plane of rotation of the drum 5.

Thus, the area subtended by the laser beam "F" between the first angular position "T1" and the second "T2" of the directing member 8 defines a circular sector in the same plane as a transversal section of the drum 5.

In other words, the direction of rotation of the laser beam "F" is substantially circumferential.

Preferably, also, the directing member 8 and the drum 5 are rotatable as one about the same axis, corresponding to the central axis "A".

Advantageously, that means there is no need for a mechanical transmission operating between the movement means 3 and the directing member 8. In effect, in this embodiment, the transmission means 9 are defined by a rigid coupling between the directing member 8 and the drum 5.

In order to make a cut which is transversal to the feed direction of the web 2, the movement means 3 are structured in such a way as to direct the feed path "P" of the web 2 around the drum 5 along a partly helicoidal line. Thus, the web 2 forms a tie around the drum 5.

More precisely, the feed unit 12 and the pick-up unit 13 of the movement means 3 are structured in such a way as to direct the web 2 (that is, the feed path "P") towards the drum 5 or to pick up the web 2 from the drum 5 at an entry angle and an exit angle substantially at right angles to the central axis "A".

The feed path "P" going in, however, is offset (that is, shifted) along the central axis "A" relative to the feed path going out.

Preferably, the extent of the shift is equal to the width of the web 2.

Thus, the drum 5 is structured to divert the feed path "P" along a helicoid until reaching a web release zone.

In other words, the drum 5 defines a guide shaped to divert the feed path "P" of the web 2 around the drum 5 itself along a portion of a helicoid extending for approximately 180°.

Advantageously, it is thus the web 2 which moves transversely relative to the laser beam "F", allowing a transversal cut to be made.

Also, in this embodiment, all the movements of the directing member (except for rotation as one with the drum 5) are eliminated, with considerable advantages in terms of costs and simplicity of design.

Also, in this embodiment, the laser beam "F" remains at all times at right angles to the cutting zone "Z", that is, to the web 2 to be cut, thus increasing process efficiency.

Preferably, the larger the entry (and exit) angle of the feed path "P" is, the smaller the circular sector "swept" (that is, covered) by the laser beam "F" between the first angular position "T1" and the second "T2" of the directing member 8.

In an alternative embodiment (FIG. 2), the constancy of the optical path travelled by the laser beam "F" between the directing member 8 and the cutting zone "Z" is obtained by curving the lateral surface of the drum 5.

Figure 2:
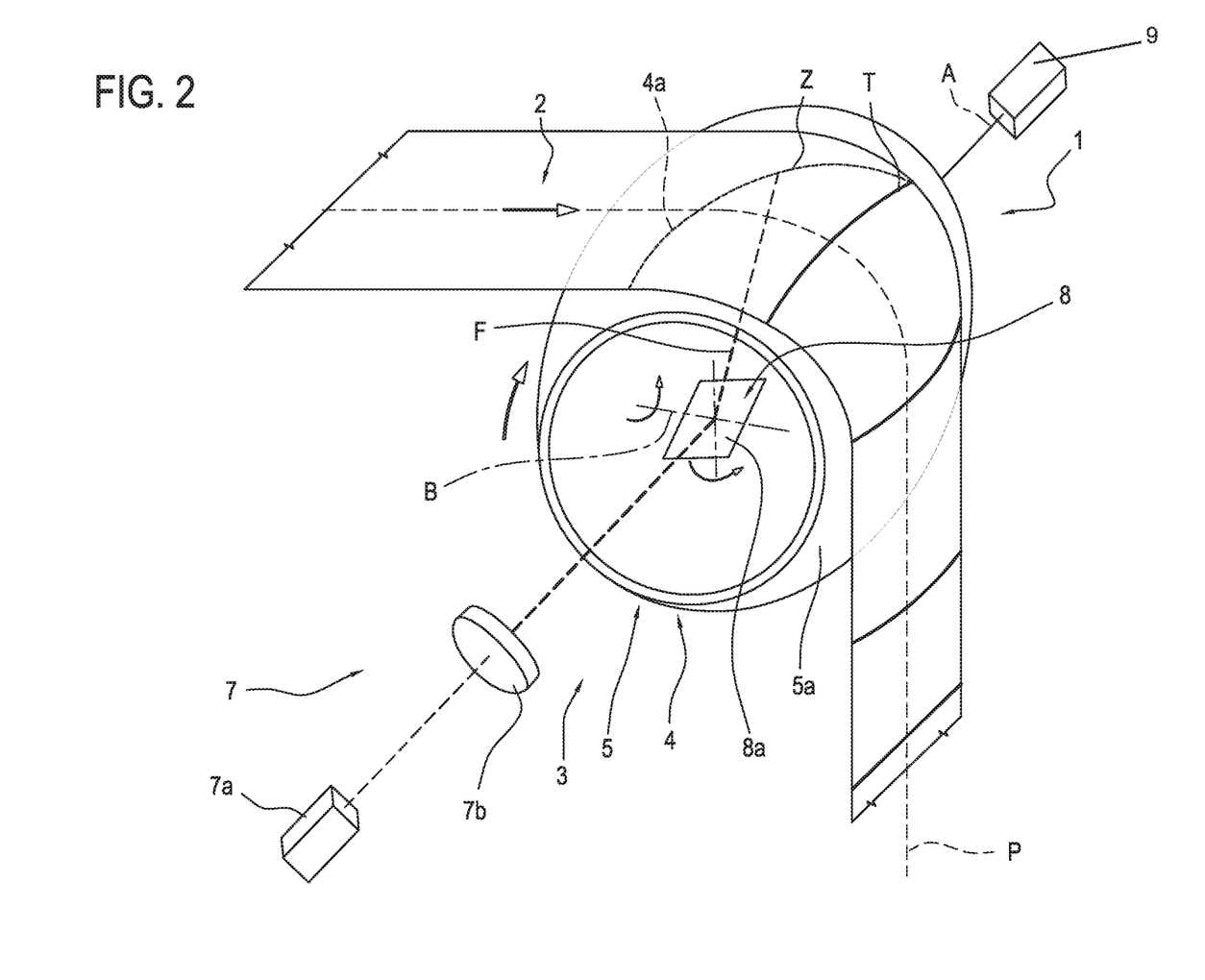
FIG. 2 shows a schematic view of a second embodiment of the device according to this invention for laser cutting a web of material.

More precisely, in some embodiments, the lateral surface of the drum 5, which constitutes a sliding surface for the web 2 (as well as the cutting zone "Z") has an at least partly spherical shape, where the directing member 8 is located at the centre of the sphere in such a way as to remain equidistant from all points of the cutting zone "Z".

It should be noted that the drum 5 can be connected removably to the conveyor 4. In other words, the drum 5 can be substituted for another of a different shape according to requirements.

The spherical surface may be obtained by keying an annular insert (at least partly spherical) on the drum 5, or by shaping the surface of the drum 5.

In this embodiment, the directing member 8 has, advantageously associated with it, motion transmission means configured to impart to it rotational motion about at least two, preferably three, axes at right angles to each other, thereby allowing complete freedom in the movement of the laser beam "F" (and thus in the geometry of the part to be made).

In a further embodiment (FIGS. 4a-4c), the conveyor 4 has a semi-elliptic guide 6a extending at least partly around the central axis "A" and a belt 6b slidable on the semi-elliptic guide 6a.

In other words, the semi-elliptic guide 6a defines for the web 2 a feed path "P" curved around the central axis "A".

This feed path "P" along the semi-elliptic guide 6a defines an elliptic line of movement.

It should be noted that the guide 6a is positioned around the central axis "A" but remains fixed relative thereto. In effect, it is the belt 6b which slides along the guide, taking the material to be cut, that is, the web 2, along with it.

In this embodiment, the directing member 8 is rotatable about its axis of rotation "B", which is incident at an angle "α" on the central axis "A".

More specifically, the value of the angle "α" is such that for each angular position of the directing member 8, the laser beam "F" intercepts a point on the semi-elliptic guide 6a located at the same predetermined distance from the directing member 8 itself.

In other words, since the guide 6a has an elliptic shape, the distance between the directing member 8 and the guide 6a, measured in a plane at right angles to the central axis "A" varies with changes in the angular position.

However, the presence of an angle "α" between the axis of rotation "B" of the directing member 8 and the central axis "A" allows the laser beam "F" to rotate in a cutting plane which is inclined at an angle to the central axis "A" and which, together with the guide 6a, defines a circle.

It should be noted that the value of the angle "α" is a function of the eccentricity of the semi-elliptic guide 6a.

More precisely, the angle "α" of inclination of the axis of rotation "B" of the directing member 8 can be calculated using the following relation:

$$\alpha a = \arcsin(e)$$

where "e" is the eccentricity of the guide 6a.

Advantageously, that way, the area subtended by the laser beam "F" between the first angular position "T1" and the second "T2" of the directing member 8, measured in a plane at right angles to the axis of rotation "B" of the directing member 8 itself, defines a circular sector perimetrically delimited by the semi-elliptic guide 6a.

The invention achieves the preset aims and brings important advantages.

In effect, the use of a directing member, that is, a mirror, mounted inside the conveyor, be it a drum or a curved guide, allows compacting the dimensions of the machine and cutting device and reducing the need to move the directing member itself.

In effect, whatever the embodiment, any variation in the distance between the directing member and the cutting zone, during the rotation of the directing member itself, is considerably reduced compared to the situation of the prior art, where the directing member was mounted outside the drum.

Moreover, linking the structure of the conveyor and of the movement means to the rotation of the directing member makes it possible to keep such distance unchanged during the entire cutting operation, that is to say, between the first and the second angular position of the directing member.

Thus, thanks to these solutions, the driving movement of the optical system and, in particular, of the directing member, is greatly reduced, if not substantially cancelled, with considerable advantages in terms of operating speed and limiting the inertias involved.

Furthermore, by combining the cylindrical shape of the drum, the tie feed system and the rotation of the directing member as one with the selfsame drum, it is possible to keep the laser beam at right angles to the cutting surface, that is, to the web, at all times, with considerable advantages in terms of process efficiency and efficacy.

The invention claimed is:

1. A device for cutting a web of material, comprising:
   a movement system by which the web of material to be cut is made to advance and defining for the web a feed path which is at least partly rotatable about a central axis; the movement system comprising a conveyor mounted around the central axis and defining an at least partly curved cutting zone;
   a laser cutting head including a laser source configured to generate a laser beam, and an optical system configured to direct the laser beam towards the cutting zone;
   wherein the optical system of the laser cutting head comprises a directing member located inside the conveyor to direct the laser beam away from the central axis towards the cutting zone; the directing member being rotatable about an axis of rotation and oriented such that the laser beam defines on the web a cutting line transversal to the feed path of the web;
   wherein the directing member is rotatable at least between a first angular, start-of-cutting position and a second angular, end-of-cutting position, and
   wherein the conveyor comprises a rotatable drum having an at least partly spherical lateral surface constituting the cutting zone and being curved both along the feed path and transversely to the feed path; the directing member being located at a center of the lateral surface so as to remain equidistant from all points of the cutting zone.

2. The device according to claim 1, wherein the conveyor includes, at the cutting zone, at least one permeable portion permeable to the laser beam and facing the directing member, so as to allow the laser beam to pass through the lateral surface.

3. The device according to claim 2, wherein the permeable portion includes a through opening.

4. The device according to claim 1, and further comprising mechanical or electro-mechanical motion transmission means operatively interposed between the movement system and the directing member to correlate a movement of the movement system along the feed path with rotation of the directing member about the axis of rotation.

5. The device according to claim 1, wherein the optical system of the laser cutting head comprises a focusing unit operatively located upstream of the directing member and able to move translationally in a straight line between a position close to the directing member, where a focal point of the laser beam is distal from the directing member, and a position away from the directing member, where the focal point of the laser beam is proximal to the directing member.

6. The device according to claim 1, wherein the directing member is rotatable about the central axis.

7. The device according to claim 1, wherein the directing member and the conveyor are rotatable as one about the same axis of rotation corresponding to the central axis.

* * * * *